(12) United States Patent
Kuramitsu

(10) Patent No.: US 8,642,804 B2
(45) Date of Patent: Feb. 4, 2014

(54) METHOD OF ADSORBING AND METHOD OF RECOVERING FLUORINE-CONTAINING COMPOUND

(75) Inventor: Masaki Kuramitsu, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 55 days.

(21) Appl. No.: 12/676,292

(22) PCT Filed: Sep. 3, 2008

(86) PCT No.: PCT/JP2008/065829
§ 371 (c)(1),
(2), (4) Date: Mar. 3, 2010

(87) PCT Pub. No.: WO2009/031562
PCT Pub. Date: Mar. 12, 2009

(65) Prior Publication Data
US 2010/0197964 A1 Aug. 5, 2010

(30) Foreign Application Priority Data
Sep. 4, 2007 (JP) ................. 2007-228684

(51) Int. Cl.
*C07C 53/21* (2006.01)
(52) U.S. Cl.
USPC ........................................ 562/605
(58) Field of Classification Search
None
See application file for complete search history.

(56) References Cited

U.S. PATENT DOCUMENTS

| | | | | |
|---|---|---|---|---|
| 4,007,116 A * | 2/1977 | Gappa et al. | ................. | 210/676 |
| 4,830,715 A | 5/1989 | Benefice-Malouet et al. | | |
| 5,705,719 A * | 1/1998 | Bloos et al. | ................. | 570/179 |
| 6,432,585 B1 | 8/2002 | Kawakami et al. | | |
| 6,991,732 B2 * | 1/2006 | Le Bec | ................. | 210/670 |
| 7,018,541 B2 | 3/2006 | Hintzer et al. | | |
| 7,641,798 B2 | 1/2010 | Yamasaki et al. | | |
| 2005/0173347 A1 * | 8/2005 | Hintzer et al. | ................. | 210/674 |
| 2007/0068869 A1 | 3/2007 | Yamasaki et al. | | |

FOREIGN PATENT DOCUMENTS

| | | |
|---|---|---|
| JP | 62-250191 A | 10/1987 |
| JP | 09-315809 A | 12/1997 |
| JP | 2003-012316 A | 1/2003 |
| JP | 2003-094052 A | 4/2003 |
| JP | 2005-44814 A | 2/2005 |
| JP | 2006-181416 A | 7/2006 |
| JP | 2007-090206 A | 4/2007 |
| JP | 2007-520350 A | 7/2007 |

OTHER PUBLICATIONS

"Carbon, Activated" in Kirk-Othmer Encyclopedia of Chemical Technology, Frederick S. Baker et al., Published Online : Aug. 15, 2003 Copyright © 1999-2011 John Wiley & Sons, Inc., pp. 741-761.*
Database CAPLUS Chemical Abstracts Service, Columbus, Ohio, US; Database Accession No. 1994:115396, Abstract of Logsdon et al., Journal of the IES (1993), 36(2), 33-36.*
Database CAPLUS Chemical Abstracts Service, Columbus, Ohio, US; Database Accession No. 1995:855924, Abstract of Kitagawa et al., Shigen Kankyo Taisaku (1995), 31(11), 941-6.*

* cited by examiner

*Primary Examiner* — Karl J Puttlitz
(74) *Attorney, Agent, or Firm* — Sughrue Mion, PLLC

(57) ABSTRACT

An adsorption process in which high adsorption of $C_2$-$C_6$ fluorine-containing compound can be attained without any morphological change thereof by the use of active carbon; and a desorption process in which active carbon and adsorbed substances can be recycled by desorption from active carbon. A liquid containing the $C_2$-$C_6$ fluorine-containing compound is brought into contact with active carbon to thereby cause the active carbon to adsorb the fluorine-containing compound and thus obtain a liquid of low fluorine-containing compound content. The active carbon having the adsorbed fluorine-containing compound is heated so as to desorb the fluorine-containing compound from the active carbon.

15 Claims, 1 Drawing Sheet

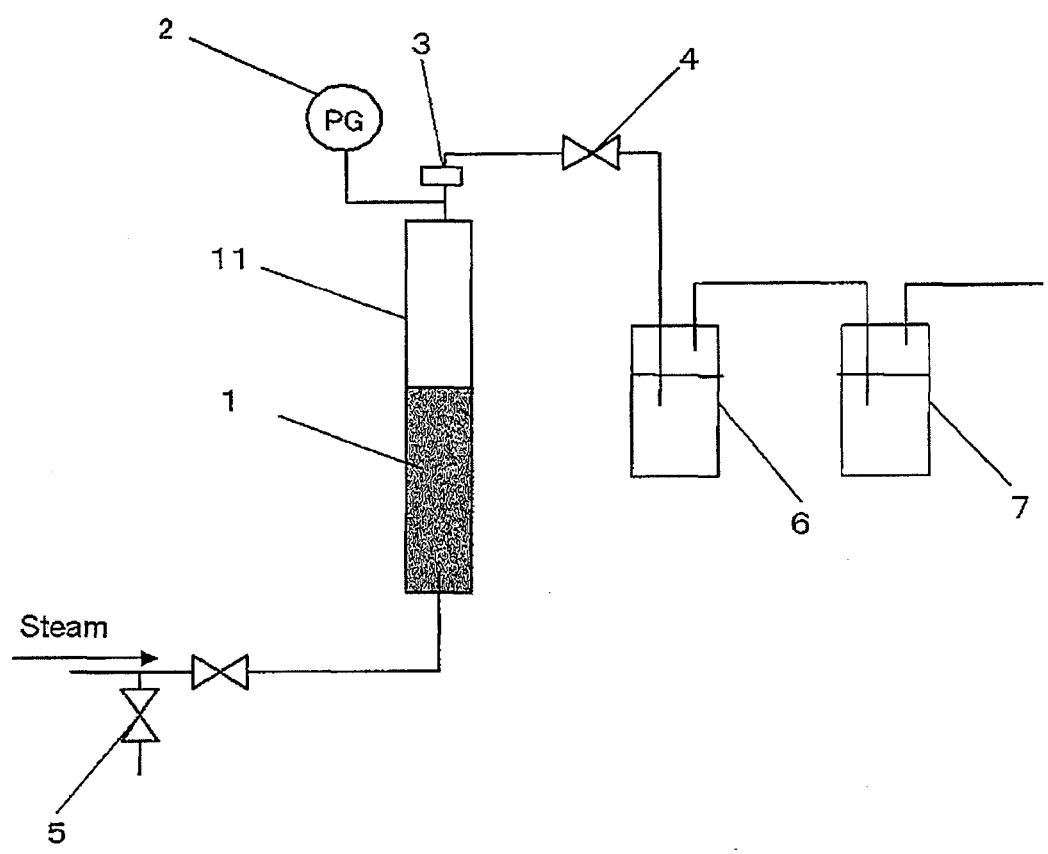

METHOD OF ADSORBING AND METHOD OF RECOVERING FLUORINE-CONTAINING COMPOUND

FIELD OF THE INVENTION

The present invention relates to a method of adsorbing a $C_2$-$C_6$ fluorine-containing compound, in which the $C_2$-$C_6$ fluorine-containing compound contained in a liquid phase is capable of highly adsorbed, and a method of recovering the $C_2$-$C_6$ fluorine-containing compound, in which the fluorine-containing compound is capable of highly recovered from an active carbon.

According to the present invention, it is capable of efficiently and selectively recovering the $C_2$-$C_6$ fluorine-containing compound from a liquid phase, such as waste water from a plant, waste water from households and rivers. In addition, it is capable of recycling active carbon and recovering the adsorbed substances by desorbing the adsorbed substances from the active carbon which has adsorbed.

BACKGROUND OF THE INVENTION

A $C_2$-$C_6$ fluorine-containing compound, for example, perfluorohexanoic acid (PFHA) has a solubility in water of about 20% at normal temperature, which is about 100 times of the solubility of perfluorooctanoic acid (PFOA) in water. Therefore, the adsorption rate of general active carbon, for example, general-purpose active carbon for waste water which was conventionally used is 5% or less at normal temperature and pH 7.

It was difficult to highly adsorb the $C_2$-$C_6$ fluorine-containing compound, which has high solubility in water, with using the conventional active carbon having a specific surface area of 1,000 m$^2$/g or less. Such adsorption method was associated with problems of cost.
Patent Document 1: JP-A-09-315809

DISCLOSURE OF THE INVENTION

Problems to be Solved by the Invention

An object of the present invention is to provide a method of highly adsorbing a $C_2$-$C_6$ fluorine-containing compound and a method of recovering the $C_2$-$C_6$ fluorine-containing compound.

Means for Solving the Problem

The present invention is based on the fact that the $C_2$-$C_6$ fluorine-containing compound is highly adsorbed by an active carbon which has been subjected to a particular treatment.

The present invention provides a method of adsorbing a $C_2$-$C_6$ fluorine-containing compound, wherein the $C_2$-$C_6$ fluorine-containing compound is adsorbed by an active carbon by contacting a liquid containing the $C_2$-$C_6$ fluorine-containing compound with the active carbon. The method of adsorbing the $C_2$-$C_6$ fluorine-containing compound may be used for a method of treating a liquid which contains the $C_2$-$C_6$ fluorine-containing compound.

The present invention further provides a method of desorbing the $C_2$-$C_6$ fluorine-containing compound, wherein the $C_2$-$C_6$ fluorine-containing compound is desorbed from the active carbon by heating the active, which has adsorbed the fluorine-containing compound, to a temperature of 150° C. or more.

It is capable to recover the $C_2$-$C_6$ fluorine-containing compound by collecting the desorbed fluorine-containing compound.

Effect Of The Invention

According to the present invention, it is capable to highly adsorb the $C_2$-$C_6$ fluorine-containing compound. In the desorbing process, it is capable to recycle the active carbon by heating the active carbon to a temperature of 150° C., which is suitable for desorption and avoids heat decomposition of the fluorine-containing compound. It is capable to recycle a $C_2$-$C_6$ fluorine-containing surfactant by collecting and concentrating the desorbed matters.

BRIEF DESCRIPTION OF THE DRAWING

FIG. 1 is a schematic view of an apparatus for desorbing active carbon, which is used in Example 3 of the present invention.

EXPLANATION OF REFERENCE NUMBERS

1: Active carbon
6, 7: Absorbing tube
11: Active carbon tube

MODE OF CARRYING OUT THE INVENTION

In the present invention, the active carbon is highly activated in order to improve the physical adsorptivity of the active carbon and the specific surface area of the active carbon is increased to 1500 m$^2$/g or more. The chemical adsorptivity of the active carbon is also improved by impregnating the surface of the active carbon with an ion. The adsorption rate of the active carbon can be improved to 10% or more, for example 20% or more.

The adsorption rate (%) is given by:

[[(Concentration of fluorine-containing compound in initial raw water [ppm])−(Concentration of fluorine-containing compound in treated water after adsorption [ppm])]×(Amount of raw water [g])]/ [(Amount of used active carbon [g])×1000,000]× 100[%].

The active carbon to be used for the present invention can be produced from carbonaceous materials. As the carbonaceous material, a material which produces an active carbon by carbonization or activation can be used. Such material includes, for example, materials of plant origin such as woods, sawn wood, charcoal, coconut shell, fruit shell such as walnut shell and seeds of fruits; materials of mineral origin, for example, coal such as peat, lignite, brown coal, bituminous coal and anthracite coal, pitch such as petroleum pitch and coal pitch, cokes, tar such as coal tar and petroleum tar, petroleum distillates residues; natural materials, for example, cellulosic fiber such as cotton and rayon, and synthetic materials such as phenolic resin, polyvinyl alcohol and polyacrylonitrile. The form of the active carbon and the carbonaceous material includes powder form, granular form, fibrous form and any form which is prepared by molding the material.

An active carbon can be produced from the carbonaceous material by subjecting the carbonaceous material to a treatment such as carbonization or activation. The carbonization may be performed by, for example, heat retorting the carbonaceous material at a temperature between about 300 and 700° C. The activation may be performed by, for example, medicament activation using, for example, zinc chloride, phosphoric acid, sulfuric acid, calcium chloride, sodium hydroxide or potassium hydroxide, gas activation using, for example, steam, carbon dioxide, oxygen gas, combustion exhaust gas or a mixture gas thereof. The size of the active carbon is generally in a range between 0.5 and 5.0 mm. Specific surface area of the active carbon can be increased by an activation. The active carbon preferably has a specific surface area of at least 1,500 $m^2/g$, for example from 1,500 to 2,500 $m^2/g$ and particularly from 1,800 to 2,500 $m^2/g$. In particular, the active carbon preferably has a specific surface area of at least 2000 $m^2/g$.

Preferably, the active carbon has an improved adsorption performance by subjecting it to a steam activation treatment. Preferably, the active carbon is exposed to a steam at a temperature of at least 120° C., for example from 130 to 350° C., particularly from 150 to 1000° C. and at a pressure of at least 0.2 MPa, for example from 0.5 to 15 MPa and particularly from 1 to 15 MPa. The treatment time of the steam activation may be generally from 10 seconds to 50 hours, for example, from 10 minutes to 10 hours. During the activation, the active carbon may be heated in a furnace.

The surface of the active carbon may be impregnated with a cation. Examples of the cation include a metal ion, a metal oxide ion and an ammonium ion. Examples of the metal include a metal atom selected from Groups 1 to 13 of the Periodic Table of the Elements, for example, an alkaline metal (for example, Li, Na and K), an alkaline earth metal (for example, Mg and Ca), and Ti, Zr, V, Cr, Fe, Ni, Cu and Zn.

Preferably, the $C_2$-$C_6$ fluorine-containing compound (that is, the fluorine-containing compound having 2 to 6 carbon atoms) is selected from carboxylic acids, particularly aliphatic carboxylic acids having an aliphatic group (particularly an alkyl group) which is partially or fully substituted with fluorine atoms. The fluorine-containing compound is preferably a compound which is represented by the general formula (1) or a salt thereof:

$$C_xF_yCOOH \qquad (1)$$

wherein x is an integer from 1 to 5 and y is an integer from 3 to 11. Examples of the salt of the fluorine-containing compound include a metal salt, an ammonium salt and an amine salt. Examples of The metal salt include a salt of an alkaline metal, for example, lithium, sodium and potassium, or a salt of an alkaline earth metal, for example, calcium and magnesium.

Examples of the fluorine-containing compound include perfluorohexanoic acid (PFHA), perfluorobutanoic acid (PFBA). Examples of the salts of the fluorine-containing compound include ammonium perfluorohexanoate salt (APFH).

The fluorine-containing compound generally has a function as a surface active agent.

In the present invention, adsorption and desorption of the fluorine-containing compound can be performed with using an active carbon. The fluorine-containing compound can be recovered by desorbing the adsorbed substances such as the fluorine-containing compound from the active carbon.

(1) Adsorption

The concentration of the fluorine-containing compound in the liquid containing the fluorine-containing compound is generally from 0.01 ppm to 20%, particularly from 10 to 100 ppm.

The liquid containing the fluorine-containing compound may be adjusted to have pH of from 1 to 5 by adding an acid, for example, an inorganic acid such as hydrochloric acid, before the adsorption.

The fluorine-containing compound is adsorbed in the active carbon by contacting the liquid containing the fluorine-containing compound with the active carbon. The temperature during the contact may be, for example, from 0 to 50° C. and the pressure may be, for example, from 0.1 to 10 atm, particularly 1 atm. The contact time may be from 0.1 seconds to 100 hours, for example, from 1 second to 1 hour, particularly from 30 seconds to 1 minute. The contact may be performed by either batch or flow process. The adsorption rate of the fluorine-containing compound to the active carbon can be controlled by changing the pH of the liquid. The pH of the liquid may be from 1.5 to 13.5, for example, from 2 to 13. The active carbon that has adsorbed can be separated from the liquid containing the fluorine-containing compound by, for example, a filtration.

(2) Desorption

Desorption of the fluorine-containing compound can be performed by heating the active carbon, which has adsorbed the fluorine-containing compound, to a high temperature, for example, at least 150° C. The temperature of the desorption may be, for example, at least 120° C., for example, from 120 to 350° C., particularly from 150 to 300° C. The pressure may be from 0.1 to 10 atm, particularly 1 atm. The heating time may be generally from 1 second to 10 hours, for example, from 1 minute to 2 hours. Steam may be used as a heating medium for applying the heat. The pressure of the steam may be generally at least 0.2 MPa, for example, from 0.2 to 15 MPa, particularly from 0.5 to 15 MPa.

(3) Recovery

The desorbed fluorine-containing compound can be recovered. Recovery of the desorbed fluorine-containing compound can be performed by collecting a steam containing the fluorine-containing compound. In order to collect the steam, the steam may be passed through water in a liquid phase, for example at a temperature of 5 to 70° C. Additionally, a vapor phase from the water in a liquid phase may be passed through an alkaline aqueous solution, for example, having a normality (N) of 0.01 to 10, particularly 0.1 to 1.0 and a temperature of 5 to 70° C.

FIG. 1 shows an apparatus to recover the fluorine-containing compound.

This apparatus has a collection tube 11 receiving an active carbon 1 (i.e. an active carbon tube), a pressure gauge 2, a filter 3, a backflow preventing valve 4, a drain valve 5, an uptake tube 6 receiving water, and an uptake tube 7 receiving an aqueous solution of 0.1N sodium hydroxide. When a steam having a pressure, for example, from 0.5 to 1.0 MPa and a temperature, for example, from 150 to 200° C. is applied to the collection tube 11 receiving an active carbon, which has adsorbed the fluorine-containing compound, the fluorine-containing compound is desorbed from the active carbon. When the steam containing the fluorine-containing compound flows through the uptake tube 6, the fluorine-containing compound is dissolved in the water received in the uptake tube 6, thereby collecting the fluorine-containing compound by the uptake tube 6. Most of the fluorine-containing compound, which has been desorbed from the active carbon, is collected by the uptake tube 6. The fluorine-containing compound, which has not collected by the uptake tube 6, can be collected by the uptake tube 7 receiving an aqueous solution of from 0.1 to 1.0 N sodium hydroxide.

Further, the collection tube 11 may be used also for adsorption of the fluorine-containing compound. After the desorption is performed, the active carbon can adsorb again the fluorine-containing compound by flowing a liquid containing the fluorine-containing compound through the collection tube. The adsorption may be performed by either batch or flow process. The batch process is generally preferable. In the batch process, the liquid containing the fluorine-containing compound is charged into the adsorption tube and is mixed with stirring the liquid, preferably with stirring the liquid and the active carbon, at a temperature of 5 to 70° C., for example 10 to 40° C., for 0.5 minute to 60 minute, for example, for 1 minute to 10 minutes.

EXAMPLES

Hereinafter, examples wherein the fluorine-containing compound in a liquid phase is adsorbed by an active carbon and examples wherein steam is applied to the active carbon which has adsorbed fluorine-containing compound ($C_2$-$C_8$ fluorosurfactant) so that the adsorbed substances is desorbed from the active carbon. In the following examples, each of six types of active carbons having different specific surface areas, which were prepared from the same material (coconut shell) was used. DIAHOPE M006 F-400 (manufactured by Calgon Mitsubishi Chemical Corporation) was used as General Carbon 1 and Shirasagi WH (manufactured by Japan Enviro-Chemicals, Limited) was used as General Carbon 2. Commercially available products such as Kuraray Coal NK-261 (manufactured by Kuraray Chemical Co., Ltd.) and active carbon manufactured by Calgon Mitsubishi Chemical Corporation were used as such or after they were activated, to be Activated Carbons 1-4.

Example 1

Into 500 cc glass bottle, each of active carbons (0.1 g) was charged and then 300 cc of aqueous solution containing 100 ppm of perfluorohexanoic acid (PFHA), which was adjusted to pH 2, was charged. The bottle was shaken at a temperature of 25° C. for 24 hours by a shaking apparatus, to adsorb perfluorohexanoic acid (PFHA) by the active carbon. Then, the equilibrium amount of adsorption was calculated. The concentrations of perfluorohexanoic acid (PFHA) in the raw water and the treated aqueous solution were compared, and the equilibrium adsorption amount of perfluorohexanoic acid (PFHA) per a unit weight of active carbon was determined. Adsorption rate of perfluorohexanoic acid (PFHA) to each active carbon is shown in Table 1.

The adsorption rate (%) is given by:

[[(Concentration of PFHA in initial raw water [ppm])–(Concentration of PFHA in treated water after adsorption [ppm])]×(Amount of raw water [g])]/[(Amount of used active carbon [g])×1,000,000]×100[%].

Accordingly, the adsorption rate (%) is represented by the equation (1) as follows:

$$[\text{adsorption rate}] = \frac{\left[\left(\begin{array}{c}\text{PFHA concentration}\\ \text{in initial aqueous}\\ \text{phase } [ppm]\end{array}\right) - \left(\begin{array}{c}\text{PFHA concentration}\\ \text{in treated}\\ \text{water } [ppm]\end{array}\right)\right] \times (\text{Amount of liquid } [g])}{\left[\left(\begin{array}{c}\text{Weight of}\\ \text{active carbon } [g]\end{array}\right) \times 1{,}000{,}000\right]} \times 100 \, [\%] \quad (1)$$

TABLE 1

| Types of Active Carbon (coconut) | Specific Surface Area [$m^2$/g] | Adsorption Rate [%] |
|---|---|---|
| Highly Activated Carbon 1 | 2300 | 26.4 |
| Highly Activated Carbon 2 | 2000 | 23.3 |
| Highly Activated Carbon 3 | 1800 | 20.6 |
| Highly Activated Carbon 4 | 1500 | 18.6 |
| General Carbon 1 | 1150 | 7.7 |
| General Carbon 2 | 1180 | 9.6 |

As shown in Table 1, the fact that there is a relationship between the adsorption rate and the specific surface area is admitted. It was also admitted that the adsorption rate of active carbons reaches 20%, when the active carbons have a specific surface area of at least 1800 [$m^2$/g.]

Example 2

The same operation as in Example 1 was repeated except for using an ion-impregnated active carbon. The PFHA adsorption rates of the active carbons classified based on the impregnated ions are shown in Table 2.

TABLE 2

| Impregnated Ion | Adsorption Rate [%] |
|---|---|
| MgO I | 14.7 |
| MgO II | 14.6 |
| Amines | 16.0 |

Example 3

An active carbon (0.1 g), to which PFHA was adsorbed until reaching the breakthrough point, was charged into an autoclave having an internal volume of 20 cc and backwashed with a steam having a temperature of 150° C. and a pressure of 0.5 MPa to 0.6 MPa for 10 minutes. The concentration of PFHA, which was adsorbed by the uptake tubes (two uptake tubes consisting of one uptake tube receiving 300 cc of water and another uptake tube receiving 300 cc of an aqueous solution of 0.1N sodium hydroxide), was determined. Then, the amount of desorption was calculated by multiplying the concentration of PFHA with the amount of the liquid. PFHA desorption effect by the steam from the active carbon is shown in Table 3.

TABLE 3

| Types of Active Carbon | Adsorption Amount [g/AC-5 g] | Desorption Amount [g/AC-5 g] | Desorption Rate [%] |
|---|---|---|---|
| Highly Activated Carbon 1 | 1.32 | 1.21 | 91.7 |
| Highly Activated Carbon 2 | 1.17 | 1.12 | 95.7 |
| Highly Activated Carbon 3 | 1.03 | 0.97 | 94.2 |
| Highly Activated Carbon 4 | 0.93 | 0.92 | 98.9 |
| General Carbon 1 | 0.39 | 0.37 | 94.9 |
| General Carbon 2 | 0.48 | 0.48 | 100.0 |

Example 4

The same operation as in Example 1 was repeated except for using PFBA (perfluorobutanoic acid) which has 4 carbon atoms. The results of the PFBA adsorption rate of the active carbons, which have various specific surface areas, are shown in Table 4.

TABLE 4

| Types of Active Carbon (coconut) | Specific Surface Area [$m^2/g$] | Adsorption Rate [%] |
| --- | --- | --- |
| Highly Activated Carbon 1 | 2000 | 43.2 |
| Highly Activated Carbon 2 | 1800 | 38.9 |
| Highly Activated Carbon 3 | 1500 | 32.7 |
| General Carbon 1 | 1150 | 29.3 |
| General Carbon 2 | 1180 | 28.9 |

Example 5

The same operation as in Example 1 was repeated using PFHA and the relationship between the pH value and the adsorption rate was determined. Adjustment of pH was performed by adding hydrochloric acid, sulfuric acid or nitric acid.

TABLE 5

| pH | Adsorption Rate [%] |
| --- | --- |
| 2.0 | 7.7 |
| 11.0 | 1.8 |

Industrial Applicability

The present invention provides an adsorption process in which high adsorption of the $C_2$-$C_6$ fluorine-containing compound can be attained without any morphological change of the $C_2$-$C_6$ fluorine-containing compound by the use of active carbon, and a desorption process in which active carbon and adsorbed substances can be recycled by desorbing the adsorbed substances from the active carbon.

Although it is not intended to limit the present invention, the $C_2$-$C_6$ fluorine-containing compound, which are contained in industrial waste water and have possibility to cause environmental problems in the future, can be highly recovered from a liquid phase and recycled according to the present invention.

The invention claimed is:

1. A method of adsorbing a fluorine-containing compound, which comprises contacting a liquid containing the fluorine-containing compound with active carbon to adsorb the fluorine-containing compound by active carbon,
wherein the active carbon has been subjected to a steam activation treatment, and
wherein the fluorine-containing compound is perfluorohexanoic acid (PFHA) or salts thereof.

2. The method of adsorption according to claim 1, wherein the active carbon is used, which has adsorption performance improved by subjecting the active carbon to a steam activation treatment.

3. The method of adsorption according to claim 1, wherein the active carbon has an adsorption rate of the fluorine-containing compound of 10% or more.

4. The method of adsorption according to claim 1, wherein the adsorption rate of the fluorine-containing compound to the active carbon is controlled by changing the pH of the liquid.

5. A method of desorbing a fluorine-containing compound, which comprises desorbing the fluorine-containing compound from an active carbon by heating the active carbon, which has adsorbed the fluorine-containing compound, to a temperature of 150° C. or more,
wherein the active carbon has been subjected to a steam activation treatment, and
wherein the fluorine-containing compound is perfluorohexanoic acid (PFHA) or salts thereof.

6. The method of desorption according to claim 5, wherein a steam having a pressure of 0.5 MPa or more at a temperature of 150° C. is used as a heating medium.

7. A method of treating a liquid containing a fluorine-containing compound, comprising contacting the liquid containing the fluorine-containing compound with an active carbon, to adsorb the fluorine-containing compound by the active carbon, whereby obtaining a liquid containing a lower amount of fluorine-containing compound,
wherein the active carbon has been subjected to a steam activation treatment, and
wherein the fluorine-containing compound is perfluorohexanoic acid (PFHA) or salts thereof.

8. A method of recovering a fluorine-containing compound, wherein the fluorine-containing compound, which was adsorbed by an active carbon, are desorbed from the active carbon by heating the active carbon to a temperature of 150° C. or more, so that the fluorine-containing compound are collected,
wherein the active carbon has been subjected to a steam activation treatment, and
wherein he fluorine-containing compound is perfluorohexanoic (PFHA) or salts thereof.

9. The method of recovery according to claim 8, wherein the absorption of the fluorine-containing compound is performed by a method which comprises contacting a liquid containing the fluorine-containing compound with active carbon to adsorb the fluorine-containing compound by active carbon.

10. A fluorine-containing compound which is recovered by a method according to claim 8.

11. The method of adsorption according to claim 1, wherein the active carbon has a specific surface area of at most 2,500 $m^2/g$.

12. The method of adsorption according to claim 1, wherein the surface of the active carbon is impregnated with a cation.

13. The method of adsorption according to claim 1, wherein the active carbon has a specific surface area of at least 1,500 $m^2/g$.

14. The method of adsorption according to claim 1, wherein the steam activation treatment comprises exposing the active carbon to steam at a temperature of at least 120° C. and a pressure of at least 0.2 MPa.

15. The method of adsorption according to claim 5, wherein the steam activation treatment comprises exposing the active carbon to steam at a temperature of at least 120° C. and a pressure of at least 0.2 MPa.

* * * * *